Figure 1:
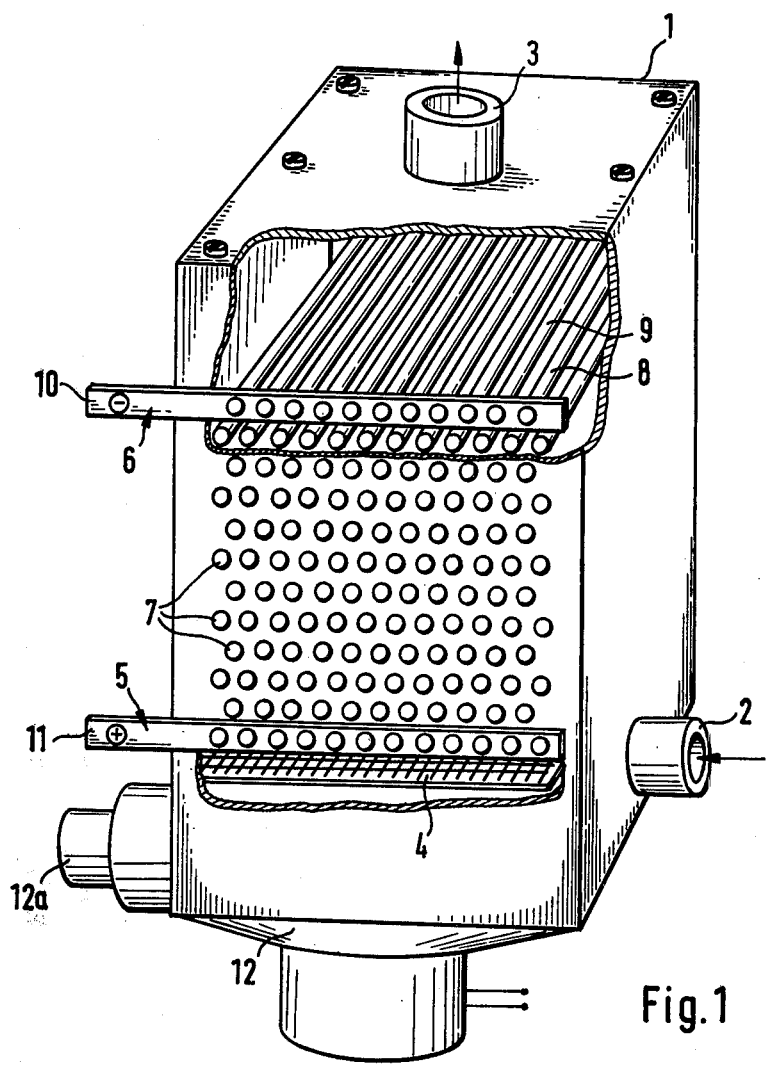

United States Patent [19]

Reis et al.

[11] 4,188,278

[45] Feb. 12, 1980

[54] APPARATUS FOR DEGERMINATING FLUIDS

[75] Inventors: A. Reis, Munich; N. Kirmaier, Aschheim; M. Schöberl, Prien, all of Fed. Rep. of Germany

[73] Assignee: Institut für Biomedizinische Technik, Munich, Fed. Rep. of Germany

[21] Appl. No.: 871,604

[22] Filed: Jan. 23, 1978

[30] Foreign Application Priority Data

Sep. 21, 1977 [DE] Fed. Rep. of Germany ....... 2742508

[51] Int. Cl.$^2$ ............................. C02B 1/82; C02C 5/12
[52] U.S. Cl. .................................... 204/268; 204/149; 204/269; 204/284
[58] Field of Search ................ 204/149, 152, 98, 222, 204/231, 235, 238, 268, 269, 273, 284

[56] References Cited

U.S. PATENT DOCUMENTS

| | | | |
|---|---|---|---|
| 3,335,078 | 8/1967 | Mehl | 204/149 X |
| 3,625,884 | 12/1971 | Waltrip | 204/149 X |
| 3,648,668 | 3/1972 | Pacheco | 204/129 X |
| 3,767,542 | 10/1973 | Carlson | 204/98 |
| 3,843,507 | 10/1974 | Kwan | 204/149 X |
| 3,865,710 | 2/1975 | Phipps | 204/152 X |
| 3,923,629 | 12/1975 | Shaffer | 204/149 X |

*Primary Examiner*—Arthur C. Prescott
*Attorney, Agent, or Firm*—Donald Brown

[57] ABSTRACT

An apparatus for degerminating fluids by the use of an electrolytic cell, a pair of main electrodes opposed in the electrolytic cell to each other, a voltage source connected to the main electrodes, and a plurality of auxiliary electrodes disposed between the main electrodes. The main electrodes are biased in such a way that the fluid flows through a region of varying potential thereby effectively increasing the degerminating rate of the cell. The main electrodes cover the entire cross section of flow, they are provided with openings to allow the passage of the fluid. The auxiliary electrodes may be connected to parts of the overall voltage thereby providing an electrolytic cell which may be directly powered by solar energy.

9 Claims, 4 Drawing Figures

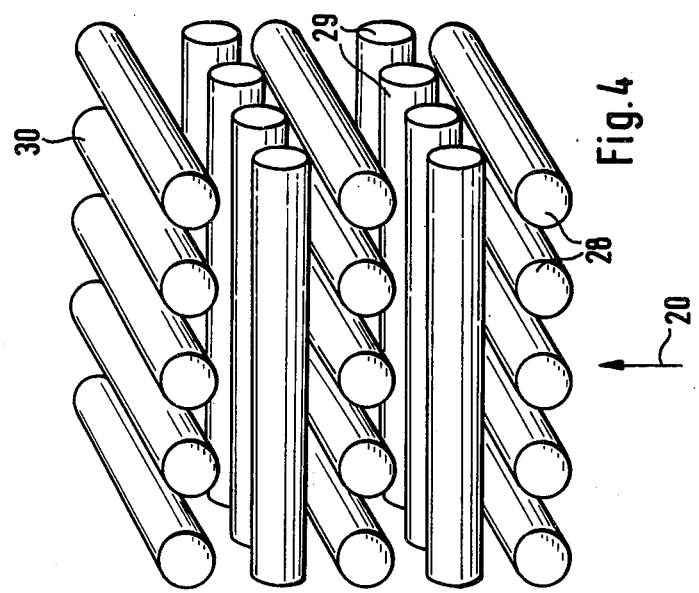
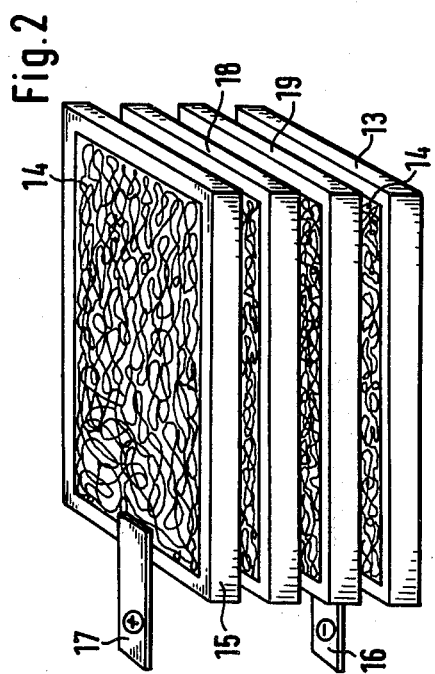
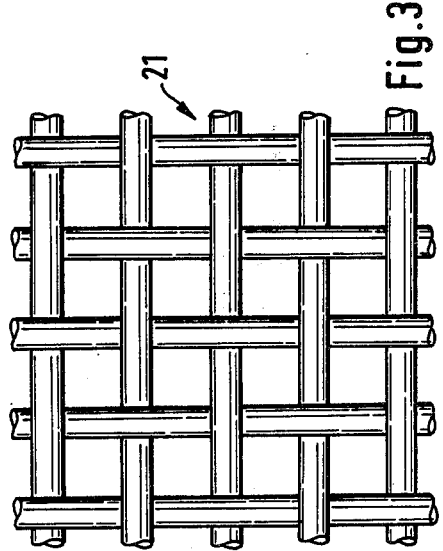

APPARATUS FOR DEGERMINATING FLUIDS

This invention relates to an apparatus for degerminating fluids by anodic oxidation employing a plurality of electrodes and auxiliary electrodes through which the liquid flows, and also a procedure for degerminating fluids by anodic oxidation.

In an apparatus for treating wastewater using an electrolytic cell described in DE-OS No. 2,324,795 (U.S. Pat. No. 3,893,900) two main elecodes are arranged parallel to the direction of flow. Auxiliary electrodes are provided in planes parallel with the main electrodes. Thus the liquid flows parallel to the electrodes. This causes dead zones between the electrode bars, and the individual bar of a plane of electrodes acts similar to a plate electrode hit by tangential flow. In this way only a small part of the fluid reaches the boundary layers of the anodes and the germs are not fully affected.

An object of the present invention is to provide an apparatus for degerminating fluids which as a high degermination rate and a highly efficient anodic oxidation.

Another object of the invention is to provide a procedure by which a high degermination rate and a highly efficient anodic oxidation may be accomplished.

According to this invention these and other objects can be accomplished by providing an apparatus wherein the electrodes are biased in such a way that the fluid flows through a region of varying potential.

The procedure to degerminate fluids by anodic oxidation according to this invention can be accomplished by letting the fluid flow through a region of varying potential and changing the direction of this varying potential.

The principle, construction and operation of this invention will be understood from the following detailed description taken in conjunction with the accompanying drawings in which FIG. 1 is a perspective view of the cell for degerminating fluids, partly showing the inside construction;

FIG. 2 another embodiment of the main- and auxiliary electrodes in a perspective view;

FIG. 3 a top view of another embodiment of electrodes arranged in a plane; and

FIG. 4 a perspective view of another embodiment of the electrodes.

According to FIG. 1 the apparatus consists of a housing 1 made of insulating plastic having an inlet 2 on the lower part of the cell housing and an outlet 3 on its upper end for the degerminated fluid.

Above the inlet 2 a sieve-shaped device 4 is arranged to streamline the fluid. In the upper space of the housing 1 a plurality of bar-type electrodes 8, 9 is provided. These electrodes may be secured to the cell wall by inserting them in holes provided therein and sealing with cement.

The electrode bars are arranged perpendicular to the direction of flow and parallel to each other, each group of electrodes is aligned in a plane, the different planes are suitably spaced. Each row of the bar-type electrodes of one plane is shifted by half the distance of two bars with respect to the bars of the following plane.

The lowermost row of bars is connected by an electrically conductive element 11 and the uppermost row by a conductive element 10. An appropriate DC-potential is applied to the elements 10, 11.

In operation of the cell the fluid, which is normally of low conductivity, is introduced through the inlet 2 into the housing 1. It flows through the sieve 4, around the main electrode 5, the auxiliary electrodes 7 and the second main electrode 6 and leaves the cell through the outlet 3.

The individual electrodes are combined to bundles having a certain ratio of distance $S_l$ to diameter d. The layers of bars or wires may be arranged as shifted or aligned or irregular bundles with the electrodes parallel or cross-wise to each other.

In the further operational description a bundle of bars arranged parallel to each other and shifted from one plane to the next is used. When the fluid flows through this bundle of shifted bars in a vertical direction high accelerating and decelarating forces are acting on the fluid along its path. In this way an intensive turbulence is caused between the individual electrode layers.

The intensity of this turbulence and thereby the mixing rate of the fluid may be expressed by the coefficient of resistance $\psi$ and the pressure loss $\Delta P$ if the Reynolds number $R_e$ is constant.

This value depends on the ratio $S_q/d$ wherein $S_q$ is the distance of two bars of diameter d in one plane. It is independent of the ratio $S_l/d$ wherein $S_l$ is the distance of two bars of diameter d from one plane to the next. This results from the fact that the coefficient of resistance is essentially determined by the amount of diverging the fluid:

$$\psi = R_e^{-0.16}\left[1 + \frac{0.47}{(S_q/d)^{1.08}}\right]$$

$$\psi \equiv \frac{\Delta P/n_l}{\delta w^2/2}$$

$$R_e \equiv \frac{w \cdot d}{\gamma}$$

Wherein $\Delta P$ is the pressure loss, w the velocity at the smallest cross section, d the diameter of a bar, $\delta$ the density and $\gamma$ the kinematic viscosity of the fluid. $n_l$ is the number of layers counted in the direction of flow.

The above mentioned equations are valid for numbers $n_l > 10$ only, otherwise the coefficient of resistance is increased.

Owing to the high flow velocity at the smallest cross sections of the bundles and the resulting intense turbulence zones behind each bar the cohesive powers of the gas bubbles on the surfaces of the bars are overcome in their initial state by the inertial force of the fluid.

This leads to a removal of the gas and a continuous activation of the electrode surface. To make the shearing forces acting on the gas bubbles effective a thin boundary layer is necessary as the gas bubbles cover the surface in a very thin layer. This is accomplished by using bars of small diameter (d = 1 ... 3 mm) because of the short path of flow perpendicular to the axis of the bar.

The intensive turbulence within the bundles also results in a good interchange of fluid at the electrode boundary layers. By using a sufficient number n of electrodes the greater part of the fluid is affected by the boundary layer.

In the apparatus described the aqueous solution and the germs contained in it are forced to pass the anodic or cathodic boundary layers thereby passing through a potential gradient of e.g. 0 to 11 Volts. As compared to electrodes of any kind hit tangentially by the fluid a higher chemical conversion ratio is attained by the described effects.

Basically it is possible to connect not only the two main electrodes 5, 6 to the necessary potentials, but also to connect each row of bar-shaped electrodes to these potentials. The advantage of a bipolar circuit like this is that the overall voltage may be reduced. If for instance tapwater is to be treated, it is necessary to apply a voltage of about 600 Volts as this fluid has a small conductivity. This voltage may be reduced to 200 Volts by using three bipolar ranges. By applying a suitable subdivision it is even possible to use very small voltages of approximately 2 or 3 Volts. In this way a degerminating apparatus according to the present invention may be built for countries with sufficient solar energy which is supplied by solar energy without any voltage transformation.

A further improvement in removing the gas bubbles may be attained by vibrating the electrodes with low frequency. For this purpose a vibrator 12 is provided at the bottom of the cell housing. The low frequency vibrations produced by this source are conducted to the electrodes by the cell walls. The vibration caused in this way reduces the adhesive forces of the gas bubbles to the electrode surface thereby facilitating the removal by the liquid flow.

In spite of the good turbulence of the apparatus described so far it is possible that carbonate deposition occurs on the cathodic face of the electrode. To prevent these depositions an ultrasonic source may be provided at the bottom of the cell housing. The vibration caused by the ultrasonic source 12 prevents the mentioned deposition. If this deposition occurs though, the potential applied to the main electrodes may be reversed periodically, for instance with a period of 15 minutes. This causes the deposit to split off thereby reactivating the entire electrode surface.

If the thin coating of an electrode bar is damaged in operation, the described way of securing the electrode bars to the cell wall facilitates the exchange of a bar, which is simply pushed out of its hole and replaced by inserting and sealing in a new bar.

It may be added that the spacing of the bars affects the economical operation of a cell as the ohmic resistance of the waste water causes dissipation. This loss can be reduced by making the spacing as small as possible. The minimum distance between the bars is determined by the medium to be treated and the pollution it contains. Obviously it is necessary to make the spacing wide enough to allow the particles flowing with the fluid to pass through the bars without clogging the cell. The spacing of the bars must therefore be wider than the maximum diameter of the particles. FIG. 2 shows another embodiment of the main- and auxiliary electrodes. Each electrode consists of a frame 13 made of conductive material and of a wire grating 14 which is electrically connected to and supported by the frame. The frames may be inserted in the cell housing after removing a wall, they are secured and spaced by insulating spacers. The outermost frames 13, 15 are connected to the electrical potential. In the embodiment shown in FIG. 2 the intermediate frames which form the auxiliary electrodes are not connected to the voltage source.

FIG. 3 shows at an enlarged scale a wire grating 21 which may be used as an electrode plane. According to this embodiment several of these frames consisting of twisted grid may be inserted in the cell housing, the voltage is applied to the outermost frames as shown in FIG. 2. The intermediate frames form the auxiliary electrodes.

In FIG. 4 another embodiment of an electrode arrangement is shown at an enlarged scale. The electrode bars 28, 29, 30 are arranged parallel to each other in one plane, the bars of the following planes are arranged perpendicular to these thus forming a cross-shaped grid. The electrode bars are secured to the cell walls and insulated according to the embodiment shown in FIG. 1. The bars 28, 30 of the outermost planes are connected by conductive elements to which the electrical potential is applied. Arrow 20 depicts the perpendicular direction of flow through these cross-wise arranged bars.

What is claimed is:

1. An apparatus for treating fluids by anodic oxidation comprising
    an electrolytic cell, having an inlet and an outlet through which said fluid flows,
    a pair of main electrodes opposed to each other in the electrolytic cell,
    a voltage source connected to the main electrodes,
    a plurality of auxiliary electrodes disposed between the main electrodes,
    each main electrode comprising a plurality of electrically connected bars which are arranged in a plane and parallel to each other,
    each auxiliary electrode comprising electrically insulated bars which are arranged in a plane and parallel to each other but whose bars are transversely shifted with respect to the bars of the adjacent electrode,
    the main electrodes providing a region of varying potential between them through which the fluid flows,
    the main electrodes located at the inlet and the outlet of the cell are substantially transverse to and cover the entire cross-section of fluid flow and are provided with openings between their bars to allow the passage of the fluid.

2. An apparatus according to claim 1, in which a vibrator provided on the cell housing transfers low frequency vibrations to the electrodes in order to remove gas bubbles from the electrodes.

3. An apparatus according to claim 1, in which the direction of the potential applied to the main electrodes is periodically reversed.

4. An apparatus according to claim 2, in which a streamlining element is provided between the inlet and the electrode zone.

5. An apparatus according to claim 3, in which an ultrasonic source is provided at the cell housing which transfers vibrations to the electrodes.

6. An apparatus according to claim 5, in which the electrodes are secured to the wall of the cell housing.

7. An apparatus for treating fluids by anodic oxidation comprising an electrolytic cell through which said fluids flow,
    a pair of main electrodes opposed to each other in the electrolytic cell,
    a voltage source connected to the main electrodes,
    a plurality of auxiliary electrodes disposed between the main electrodes,
    the main electrodes on the inlet and the outlet side of the cell cover the entire cross-section of flow and are provided with openings to allow the passage of the fluid, and the main electrodes comprise a pressed wire grating which is electrically connected to and supported by a frame.

8. An apparatus according to claim 7, in which the direction of the potential applied to the main electrodes is periodically reversed.

9. An apparatus according to claim 8, in which at least one vibrator provided on the cell housing transfers low frequency vibrations to the electrodes in order to remove gas bubbles from the electrodes.

* * * * *